United States Patent [19]

Grundy

[11] Patent Number: 4,925,474
[45] Date of Patent: May 15, 1990

[54] METHOD AND APPARATUS FOR ON-LINE LOI MEASUREMENT OF FIBERS

[75] Inventor: Reed H. Grundy, Murrysville, Pa.

[73] Assignee: PPG Industries, Inc., Pittsburgh, Pa.

[21] Appl. No.: 425,145

[22] Filed: Oct. 23, 1989

Related U.S. Application Data

[63] Continuation-in-part of Ser. No. 281,140, Dec. 7, 1988, abandoned.

[51] Int. Cl.$^5$ .................. C03B 37/07; C03B 37/12; C03C 25/02
[52] U.S. Cl. .................................. 65/29; 65/3.1; 65/10.1; 65/161; 34/89; 324/694
[58] Field of Search .............. 65/2, 3.1, 10.1, 29, 65/161; 73/160; 324/65 R; 34/89

[56] References Cited

U.S. PATENT DOCUMENTS

| | | | |
|---|---|---|---|
| 2,702,948 | 3/1965 | Seney | 324/65 R X |
| 3,539,324 | 11/1970 | Terakado et al. | 65/29 X |
| 4,253,243 | 3/1981 | Whelan | 34/89 X |
| 4,321,072 | 3/1982 | Dubos et al. | 65/10.1 X |
| 4,501,492 | 2/1985 | Douklias | 65/29 X |
| 4,717,870 | 1/1988 | Vuncannon | 324/65 R X |
| 4,761,638 | 8/1988 | Lozano | 324/65 R X |
| 4,817,021 | 3/1989 | Sowerby et al. | 324/65 R X |

Primary Examiner—Robert L. Lindsay
Attorney, Agent, or Firm—John E. Curley

[57] ABSTRACT

A method and apparatus constructed to measure the fluid present in a multifilament or fiber strand moving at high speed is described and involves conductive contact points along the strand path which contact the strand and generate signals. The signals which are conductance measurements are synchronously demodulated to produce a signal representing the volume of fluid in the strand.

9 Claims, 2 Drawing Sheets

METHOD AND APPARATUS FOR ON-LINE LOI MEASUREMENT OF FIBERS

This patent application is a continuation-in-part application of U.S. Ser. No. 07/281,140 filed Dec. 7, 1988 abandoned.

The present invention relates to the measurement of the volume of fluid present on a fiber bundle that is moving at high speed. More particularly the present invention relates to the measurement of the LOI on a bundle of fibers that have a fluid coating or binder thereon. Still more particularly the present invention relates to the measurement of the LOI on a binder or size present on a moving bundle of glass fibers.

BACKGROUND OF THE INVENTION

In the preparation of strands, threads, yarns and the like (hereinafter "bundles") it is often required that the fibers, which make up the bundles, be coated or treated with an appropriate size or binder to impart to the finished bundle certain desired properties. Thus, for example, in the preparation of a bundle of glass fibers that are to be used to reinforce a resin matrix it is common practice to place on the fibers that form the bundle a binder that will impart to the glass fiber bundle an affinity in the bundle to firmly bond the glass bundle reinforcement to the resin matrix that is being reinforced. The binders or sizes used are applied by spray devices, pads and in the case of glass fibers most commonly from the surface of applicators of the roller or belt type. Regardless of the apparatus used to place the binder or size on the fibers making up a bundle, the amount of that size or binder can vary over a wide range depending on circumstances. The quantity of binder or size can often be a critical factor in determining whether or not a given bundle is satisfactory for its intended use. In determining what that quantity is, a large length, typically 120 yards of the bundle to be tested in the case of a fiber glass bundle, is collected and weighed. The bundle is then subjected to the application of heat to burn off the binder material therein, and it is then subjected to further weighing. The difference in the weights obtained is the LOI of the bundle when it is divided by the original weight and multiplied by 100.

As will be appreciated by the skilled artisan, this is a costly and time consuming test and in many instances provides information that is of little practical value since, if corrections need to be made to the manufacturing process, they are made only after many yards of defective materials have been formed. In many instances where the LOI for a given fiber bundle exceeds that of the specification for the product but does not interfere with the performance of the product, that excess represents increased manufacturing costs while not providing any benefit to the user. This is an unacceptable practice for the manufacture if it can be controlled or avoided. The difficulty in making the rapid measurements necessary to address the problems referred to reside in the fact that the fibers which constitute the bundles have the binder applied to them as they are being formed and the bundles are moving as they are formed at high speeds. By "high speeds" as used herein in the specification is meant a linear movement of the bundles typically speeds of 2,500 to 20,000 feet per minute or more. The binders and sizes are added to the fibers usually as they pass over an applicator or through the spraying zone as the case may be while they are moving at high speed and it is difficult to ascertain the accuracy of the application of the material to the fibers without going through the time consuming weighing procedure which has been described generally above.

Thus, a need exists for a reliable and rapid method and apparatus for determining the LOI on bundles being produced from a plurality of fibers. This need is especially required in the formation of fibers used to form glass fiber bundles to assess accurately the operation of the applicators in that art and their effectiveness in delivering to the fibers the desired or required amount of binder or size. The instant invention satisfies these needs.

SUMMARY OF THE INVENTION

In accordance with the instant invention a process is provided which involves testing fiber in bundle form while they are moving at high speed to determine the volume of binder or size present in a given length of the bundle being tested. The bundle being tested is thus passed at the speeds it is being processed across the surface of a first and a second electrically conductive element. The two conductive elements are spaced from each other a fixed distance and the strand length measured is the length of the bundle located between the two electrically conductive members the surfaces of which the bundle is contacting as it travels. The bundle as it touches the two conductive elements generates a signal which represents the voltage drop between the strands contact with the two conductive elements. This signal in accordance with this invention is then synchronously demodulated, and a new signal is generated. This second signal represents the volume of fluid in the bundle between the two conductive elements and can be recorded as such or reported as percent LOI on the bundle. In the preferred system the method involves passing the bundle over a first and a second electrical contact and generating a first signal representing the voltage drop across those two elements. The bundle is then passed over a third electrical contact, and the signal that is generated between the second and the third contact element represents the voltage drop between those two points. The two signals so generated are then synchronously demodulated to thereby produce a third signal which is representative of the volume of the fluid in the bundle between the first and the third contact point for the bundle.

DETAILED DESCRIPTION OF THE INVENTION

Figure 1:
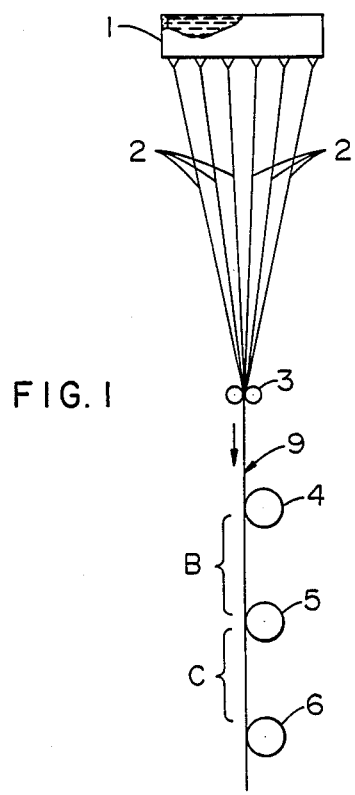
FIGS. 1 and 1a show a fiber forming bushing and strand made by this invention.
Figure 1A:
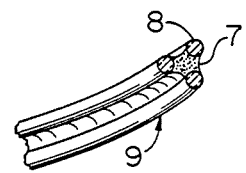

FIG. 1 is composed of a fiber forming bushing 1 out of which is drawn fibers 2 through a applicator device, gathering device 3 and onto the winder unshown. The strand passes over three electrodes 4, 5 and 6. The strand 9 is composed of a binder 7 which is within the interstitial space of the round glass filaments 8 as shown in the insert.

Figure 2:
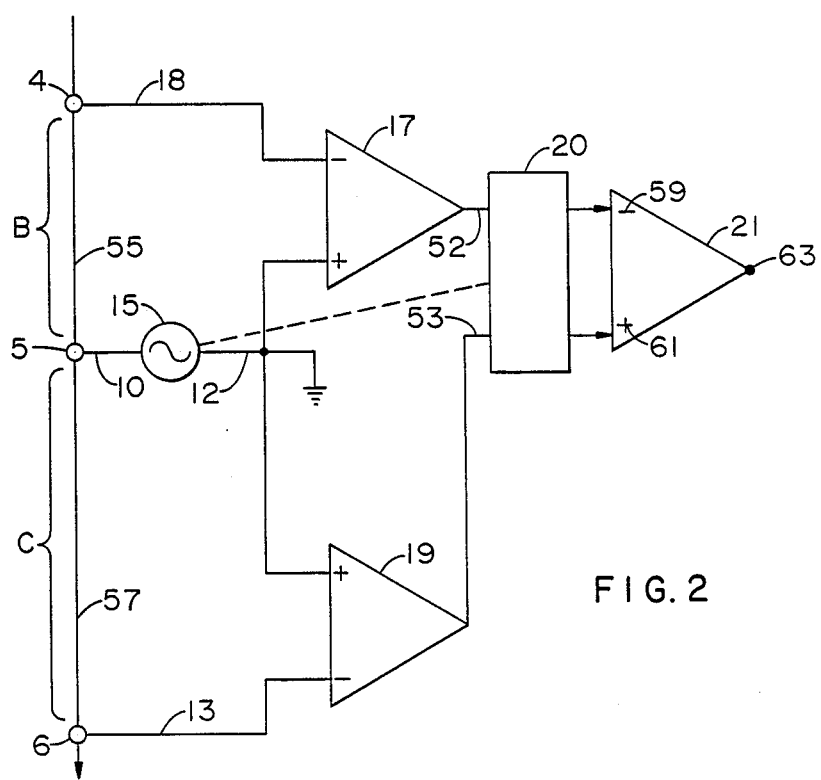
FIGS. 2 and 3 show schematic block diagrams of the invention.

FIG. 2 is an electronic block diagram of my invention. The electrodes 4, 5 and 6 contact the strands for purposes of applying voltage and detecting current.

The voltage is applied to the center electrode 5 and passes to electrodes 4 and 6 which form the input to amplifiers 17 and 19. The purpose of the circuit depicted by FIG. 2 is to measure the resistance of the filament strand or bundle between the electrode 4 and 6. Due to the electronic nature of the surface of the glass, extraneous voltages of a random nature will be sensed by all three electrodes. For this reason the circuit which is used in FIG. 2 is specifically of a type used where a large noise voltage with respect to the signal voltage exists. Such a circuit is known as a phase sensitive demodulator. The phase sensitive demodulator depicted in FIG. 2 works by supplying a alternating potential to the electrode 5 through wire 10. The alternating potential 15 is kept in unison with a switching network 20. When the potential at pin 5 is positive, a positive current flows through the filament bundle and its associated binder chemistry through pin electrode 4 whereupon it is inverted and amplified by amplifier 17. After passing through amplifier 17 the signal appears as a negative voltage on conductor 52. The phase sensitive demodulator switch 20 which is in synchronism with the current source 15 passes the negative signal from amplifier 17, conductor 52, into the negative input 59 of amplifier 21. In a similar manner when the oscillating voltage of the source 15 is negative, the output 52 of amplifier 17 is then positive whereupon the phase sensitive detector has switched so that the output conductor 52 is then routed to input 61, the positive input of amplifier 21. By switching the input 52 between the positive and negative inputs of amplifier 21 the output 63 of amplifier 21 is always positive. In a similar manner the phase sensitive demodulator also switches the output 53 of amplifier 19 so that it also produces an output on conductor 53 which is connected to the positive input 61 of amplifier 21. Input 61 being of opposite sign to that of input 59 then produces twice the output 63 of amplifier 21.

As mentioned above, there exists a noise source between the electrodes 4, 5 and 6. The noise source is time varying in a random manner. Because of the random nature of noise source 55, the signal appearing on output 52 is likewise random in nature. If the frequency of the random fluctuation is greater than the switching frequency of the phase sensitive demodulator 20, then the signal appearing at pin 63 of amplifier 21 will have a mean of zero and, therefore, be ignored with regard to the much larger positive measured signal. Conversely, if the fluctuations of the noise source are slower than the switching frequency of the phase sensitive demodulator 20, the signal appearing at the output 63 of amplifier 21 will again be substantially zero provided that the switching period of the phase sensitive demodulator 20 is of a 50/50 nature. Thus, it can be appreciated that by using the phase sensitive demodulator shown in FIG. 2 the signal at output 63, resulting from the voltage source 15 is much larger than signal due to the noise sources 57 and 55.

Figure 3:
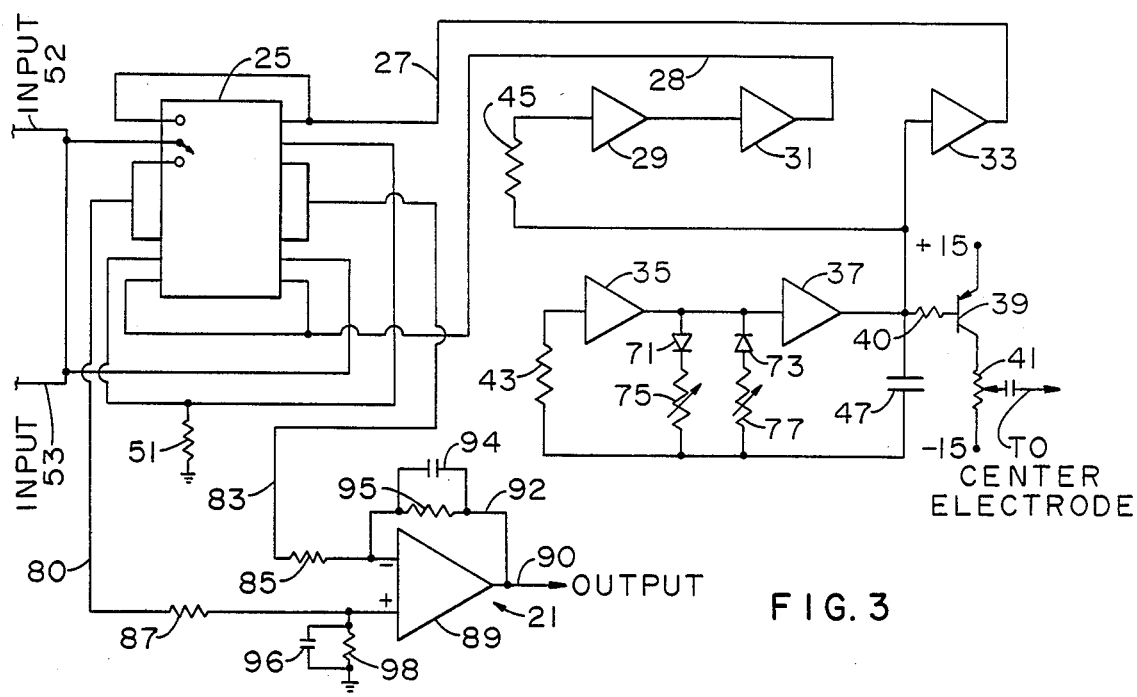

FIG. 3 is a schematic diagram of block diagram shown in FIG. 2. It consists of a phase sensitive detector 25 and the output amplifier 21 of FIG. 2. Also included in FIG. 3 is the voltage source 15 of FIG. 2. The voltage source 15 of FIG. 2 is composed of transistors Q1, 39, base resistor 40 and collector resistor 41. Collector resistor 41 is a potentiometer which allows adjustment of the level of voltage that is fed to the center electrode 5. Portions of a hex inverting buffer amplifier 35 and 37 are connected as a multivibrator. Diodes 71 and 73 allow independent operation of the time constant formed by capacitor 47 and resistors 75 and 77. This independent operation makes possible an adjustment of the duty cycle to 50 percent on and 50 percent off. The output of the oscillator is fed to buffer 33 for the in phase component and through two inverting stage buffers 29 and 31 for the out of phase component. These in and out of phase components are then fed over conductors 27 and 28 to the inputs of a switch 25. Thus, the transfer contacts (solid state equivalent) are controlled by in and out of phase signals arriving over conductors 27 and 28. The input to the switch via conductors 52 and 53 is then synchronously demodulated by switch 25 and output through conductors 80 and 83. The signals on 83 and 80 are of opposite polarity having been synchronously demodulated by the demodulator 25 whereas the noise is substantially zero. The circuit formed by amplifier 89 and associated circuitry forms a low pass filter which removes the demodulating frequency. The output appearing at conductor 90 is essentially DC voltage inversely proportional to the average of resistance 141 and 143. Resistance 141 and 143 are inversely proportional to the amount of binder 7 shown in the inset of FIG. 1. Therefore, the voltage at output 90 is directly proportional to the amount of binder 7 of strand 9, said amount otherwise known as binder LOI (loss of ignition).

Figure 4:
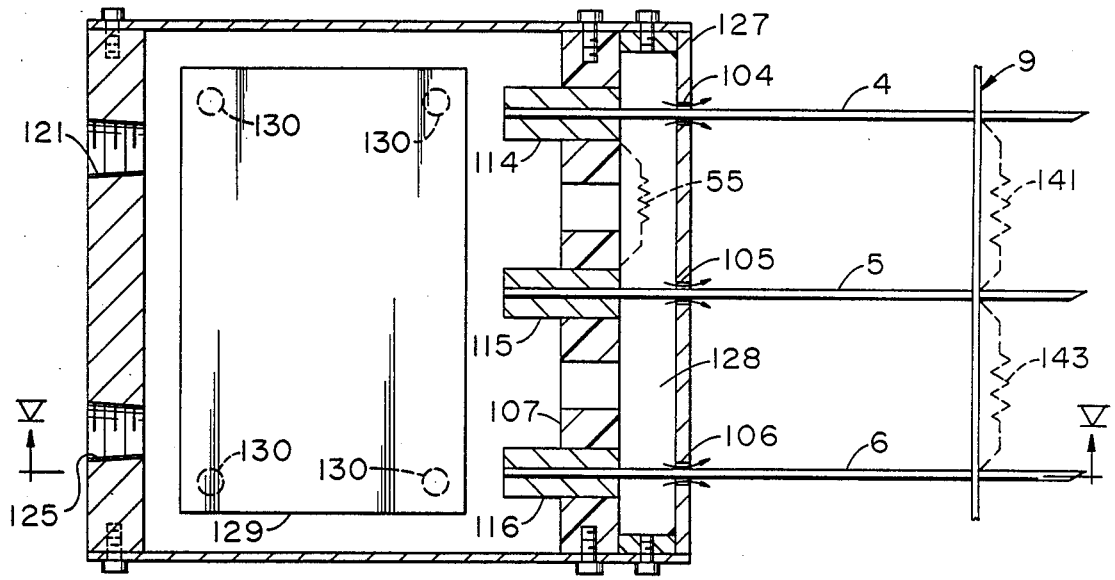
FIGS. 4 and 5 are mechanical views of the embodiment of the invention.
Figure 5:
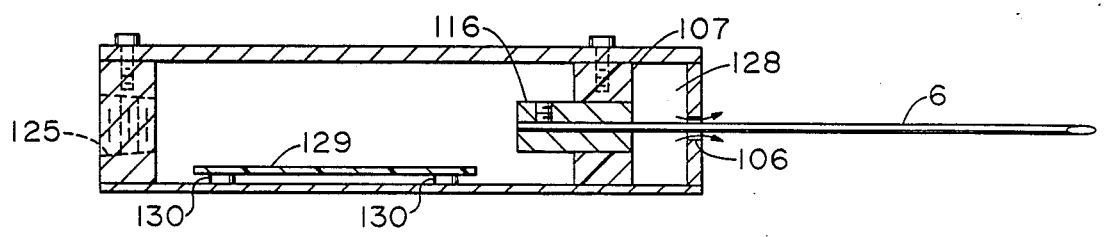

FIG. 4 and FIG. 5 are mechanical views of the embodiment of my invention. In my device electrodes 4, 5 and 6 are held in conductive receptacles 114, 115 and 116. The electrodes are positioned by a nonconducting piece 107 such that they pass through holes 104, 105 and 106 in a concentric manner so as to not tough the edges. The strand 9 contacts the electrodes 4, 5 and 6 with its inherent, internal resistance 141, 143 to be measured. The measurement of resistance 141 and 143 would be adversely affected if the binder was permitted to contact and form a leakage path from electrodes 4 to 5 and 5 to 6. This phenomena is prevented by the concentric holes which have a pressurized gas supplied to the backside of the holes through threaded adapters 121 or 125. This escaping gas removes any water which would contact electrodes 4, 5 and 6 and also prevents water or conducting fluid from entering into the chamber 128 and impinging upon the insulating surface 107. By this arrangement any leakage resistance 55 in parallel with strand resistance 141 as a result of moisture contamination is eliminated.

It will be appreciated by those skilled artisans that the apparatus claimed herein constitutes a sensor. This sensor is capable of continuously measuring the amount of binder that is applied to a moving strand as it is produced. It is possible, therefore, to use the sensor in conjunction with the binder applicator to closely regulate the amount of binder that is applied to the strand. This is accomplished by using an operational amplifier (not shown) to compare the output signal of the sensor with a signal representative of the desired binder LOI being produced. The resultant signal produced by this comparison is then used to control the amount of binder being applied by adjustment of applicator belt speed or applicator pump speed. By connecting the sensor and applicator in a continuous feedback scheme, the product LOI is continuously controlled.

The above description of the drawings has illustrated the invention with respect to a fiber glass forming operation and fiber glass bundles of fibers, but it will be understood that the invention has applicability to any fiber forming operation where fibers are gathered into bundles and coated with sizes, binders or coatings, and it is desired to control the content of those sizes, binders and coatings. Thus, synthetic fibers, such as organic polymeric fibers (polypropylene, polyesters, nylons, and the like being typical nonexclusive examples), natural fibers (cotton, wool and linen being typical nonexclusive examples) and inorganic fibers (graphite, boron and silica being typical nonexclusive examples) and mixtures of such fibers are also within the contemplation of the invention.

In general, the fibers measured for LOI in bundle form are nonconductive and the liquid coatings, sizes and binders are electrically conductive. However, while the liquid in the interstices of the fibers forming the bundles is always conductive to some extent so that the measurements can occur, the fibers per se can also be conductive. Thus, the fibers forming the bundles measured by the instant invention can be conductive or nonconductive. If the fibers in a given bundle have conductive properties prior to being sized or coated, it will be necessary to ascertain that conductivity. This can be done by subjecting the bundle to the same measurements as a coated bundle before the application of the coating, determining the conductivity of the bundle, coating the fibers and determining the second conductance. The first measured conductance subtracted from the second measured conductance will then determine the LOI. This last calculation can be easily done electrically and continuously and is within the skill in the art.

While the invention has been described with respect to certain specific embodiments, it is not intended that it be limited thereby except insofar as appears in the accompanying claims.

I claim:

1. A method of measuring the volume of electrically conductive liquid present on a fiber bundle which is travelling at high speed along a path comprising contacting the bundle with a first and a second conductive element speed apart from each other along the fiber bundle path, producing a signal representative of the voltage drop along the bundle between the two said elements, contacting the bundle with a third conductive element spaced from the second element in the fiber bundle path and producing a signal representative of the voltage drop between the second and the third element, synchronously demodulating the first and second signals so produced to produce a third signal representing the volume of the said liquid in the fiber bundle length between the first and the third conductive element.

2. The method of claim 1, wherein the noise appearing between the first and second conductive elements and between the second and third conductive elements is reduced to substantially zero.

3. A method of measuring the volume of electrically conductive liquid present on a fiber bundle travelling at high speed along a path comprising contacting the bundle with a first and a second conductive element, said elements being spaced apart a fixed distance, generating first a signal representative of the voltage drop along the fiber bundle between said conductive elements synchronously demodulating the signal so generated to produce a second signal representative of the volume of said liquid in the fiber bundle length contacting the conductive elements and generating the first signal.

4. The method of claim 3, wherein the noise appearing between the conductive elements is reduced to substantially zero.

5. An apparatus for measuring the volume of electrically conductive fluid on a moving bundle of fibers comprising electrically conductive first and second means spaced from each other and positioned in the path of travel of said moving bundle so that the bundle contacts each said conductive means, means to pass current representing the voltage drop across the bundle between the first and second electrically conductive means to a first amplifier, means to pass the signal from the first amplifier to a phase sensitive demodulator, second amplifier means connected across the output of said demodulator and a voltage source connected to said second conductive means, and operatively in phase with the demodulator and driven thereby.

6. A method of measuring the volume of electrically conductive fluid present in a glass fiber bundle containing a multiplicity of glass fibers which are travelling at high speed along a path comprising contacting the said glass fiber bundle with a first and a second conductive element spaced apart from each other along the fiber bundle path, producing a signal representative of the voltage drop along the bundle between the two said elements, contacting the glass fiber bundle with a third conductive element spaced from the second element in the glass fiber bundle path and producing a signal representative of the voltage drop between the second and the third elements, synchronously demodulating the first and second signals so produced to produce a third signal representing the volume of the said liquid in the first fiber length between the first and the third conductive element.

7. The method of claim 6, wherein the noise appearing between the first and second conductive elements and between the second and third conductive element is reduced to substantially zero.

8. In a glass fiber forming process wherein molten glass is drawn into a plurality of glass fibers and the fibers are coated with an electrically conductive liquid and gathered into strand form at high speed and collected or processed as strands, the improvement comprising measuring the volume of said liquid present on the glass fiber strand travelling at high speed along a path involving contacting the glass fiber strand with a first and a second conductive element, said elements being spaced apart a fixed distance, generating first a signal representative of the voltage drop along the glass fiber strand between said conductive elements and synchronously demodulating the signal so generated to produce a second signal representative of the volume of said liquid in the glass fiber strand length contacting the conductive elements.

9. The method of claim 8, wherein the noise appearing between the conductive elements is reduced to substantially zero.

* * * * *